United States Patent

Pappas et al.

[11] Patent Number: 5,868,797
[45] Date of Patent: Feb. 9, 1999

[54] PROSTHESIS FIXTURING DEVICE

[75] Inventors: Michael J. Pappas, Stuart; Frederick F. Buechel, Naples, both of Fla.

[73] Assignee: Biomedical Engineering Trust I, N.J.

[21] Appl. No.: 587,932

[22] Filed: Jan. 17, 1996

Related U.S. Application Data

[62] Division of Ser. No. 330,196, Oct. 27, 1994, abandoned.

[51] Int. Cl.⁶ .......................................... A61F 2/38
[52] U.S. Cl. ................................................ 623/20
[58] Field of Search ................................. 623/20

[56] References Cited

U.S. PATENT DOCUMENTS

| | | | |
|---|---|---|---|
| 3,868,730 | 3/1975 | Kaufer et al. | 623/20 |
| 4,257,128 | 3/1981 | Scales | 623/20 |
| 4,936,847 | 6/1990 | Manginelli | 623/20 |
| 4,938,769 | 7/1990 | Shaw | 623/20 |
| 4,985,037 | 1/1991 | Peterson | 623/20 |
| 5,047,058 | 9/1991 | Roberts | 623/18 |
| 5,152,797 | 10/1992 | Luckman | 623/20 |
| 5,207,711 | 5/1993 | Casparl | 623/20 |
| 5,246,459 | 9/1993 | Elias | 623/18 |
| 5,290,313 | 3/1994 | Heldreth | 623/18 |
| 5,370,701 | 12/1994 | Finn | 623/20 |

*Primary Examiner*—Michael J. Milano
*Attorney, Agent, or Firm*—Anthony J. Casella; Gerald E. Hespos; Ludomir A. Budzyn

[57] ABSTRACT

A tibia fixturing device comprises a metal tray formed with annularly spaced recesses in its underside at a depth of at least about 1.5 mm and from which a stem depends for axial insertion into a tibia conical cavity. The stem has a circular cylindrical portion proximal the tray and a conical portion distal the tray. Fins radially extend from the stem cylindrical portion and penetrate the tibia to provide some torsional resistance. Axially extending channels are formed about the stem periphery which channels have bottom surfaces parallel to the stem axis to provide further torsional resistance. The channels are arranged to not interlock with the cement in the axial direction to permit the cement to separate first from the device during axial removal of the device from the bone. The fins have inclined edges distal the tray and inclined radial outer edges to align and center the stem to the bone cavity edge. Cement in the tray recesses bonds the tray to a tibia resected surface to provide major torsional resistance of the tray about the cavity longitudinal axis.

10 Claims, 4 Drawing Sheets

PROSTHESIS FIXTURING DEVICE

This applications is a division of application Ser. No. 08/330,196 filed Oct. 27, 1994 which application is now abandoned.

BACKGROUND

This invention relates to prothesis fixturing devices, more particularly, fixturing stems for attaching a prothesis to a bone, e.g., a tibia, and a prothesis with an articulating bearing surface.

Many methods have been employed to fixture prostheses to bone, including screws, press fit, bone cement and biological fixation into porous surfaces. Currently bone cement and biological ingrowth are the preferred means of fixation. Fixturing surface geometries used include plates, fins, stems and pegs of various cross-sections. Fins form projections which in the prior art need bone preparation such as mating slots in the bone to receive the fins. This is undesirable as it entails further surgical procedures in addition to the prescribed procedures for preparing the bone for a tapered stem without such fins. Reference is made, for example, to brochures nj LCS® Tricompartmental Knee System with Porocoat®, Surgical Procedure by Frederick F. Buechel, 1993, Biomedical Engineering Trust, South Orange, NJ and Biomechanics and Design Rationale; New Jersey LCS® Knee Replacement System by Michael J. Pappas et al. 1993, Biomedical Engineering Trust which illustrate fixturing geometries and procedures for knee prosthesis.

The problem in these protheses is to securely attach a prothesis to bone, and yet permit the prothesis to be removed from the bone without damage thereto. More particularly, a problem is known in using cement with such protheses. For example, if the cement interlocks with depressions in the mating prothesis surface, then such interlocking may cause bone damage when the prothesis is removed. Such removal is sometimes necessitated by failure or otherwise degeneration of the prothesis-bone configuration.

Another problem encountered during the insertion procedure in attaching the prothesis via a fixturing device to the bone is alignment. Known fixturing stems are different shapes including conical, rectangular, fin among others. The mating bone cavity is similarly shaped as the corresponding stem. There is a gap between these elements when engaged to accommodate cement. These elements need to be axially aligned during the insertion process. The gap could cause misalignment of the elements during insertion or later during curing of the cement. Any misalignment could cause problems with the user of the joint, especially a knee prosthesis where motion directions can be critical. Thus, it is important that the mating elements remain fixed in place and properly aligned during insertion and curing of the cement.

A still further problem is loosening of the prothesis from the bone to which the prothesis is attached during use.

The present inventor recognizes a need for improving torsional resistance between the fixturing device and the bone to which the device is attached, stability during curing of the cement or biological ingrowth, and ease of implantation and removal the device in the event of failure.

A prothesis fixturing device according to one embodiment of the present invention attaches a prothesis component including a bearing to a bone, the bone having a resected surface. The device is subject to torque loads about an axis transverse the resected surface, the torque loads tending to loosen the device relative to the bone. The device comprises a tray having a first surface for receiving the bearing and a second opposing surface and at least one wall depending from the opposing second surface for abutting the resected surface and for forming at least one recessed compartment with the second surface at a depth of at least 1.50 mm to receive a cement for bonding the tray to the bone at the resected surface, the at least one wall having a configuration for providing resistance to torque loads on the tray about the axis.

In a further embodiment a prothesis fixturing device attaches a prothesis component including a bearing to a bone, the bone having a resected surface and a cavity defining a longitudinal first axis transverse the surface, the cavity being in communication with the surface at a cavity edge, the surface and cavity for receiving the device. The device comprises a stem for receiving a prothesis and defines a second longitudinal axis. Centering means are integral with the stem forming a one piece construction for engaging the cavity edge to center the stem relative to the cavity first axis during axial insertion of the stem into the cavity.

In accordance with a further embodiment the stem has a plurality of axially extending channels having a bottom surface, the stem having a peripheral surface, the channel bottom surfaces intersecting the stem peripheral surface at a channel region distal the tray, the bottom surfaces each having a radial dimension to the second axis at least as great as the radial dimension of the intersections.

A stem according to a still further embodiment depends from a tray and defines a second longitudinal axis, the stem being dimensioned for insertion into the cavity with the axes substantially parallel, the stem having a cylindrical axially extending portion proximal the tray and a conical portion axially extending from the cylindrical portion distal the tray.

DESCRIPTION OF THE PREFERRED EMBODIMENTS

Figure 1:
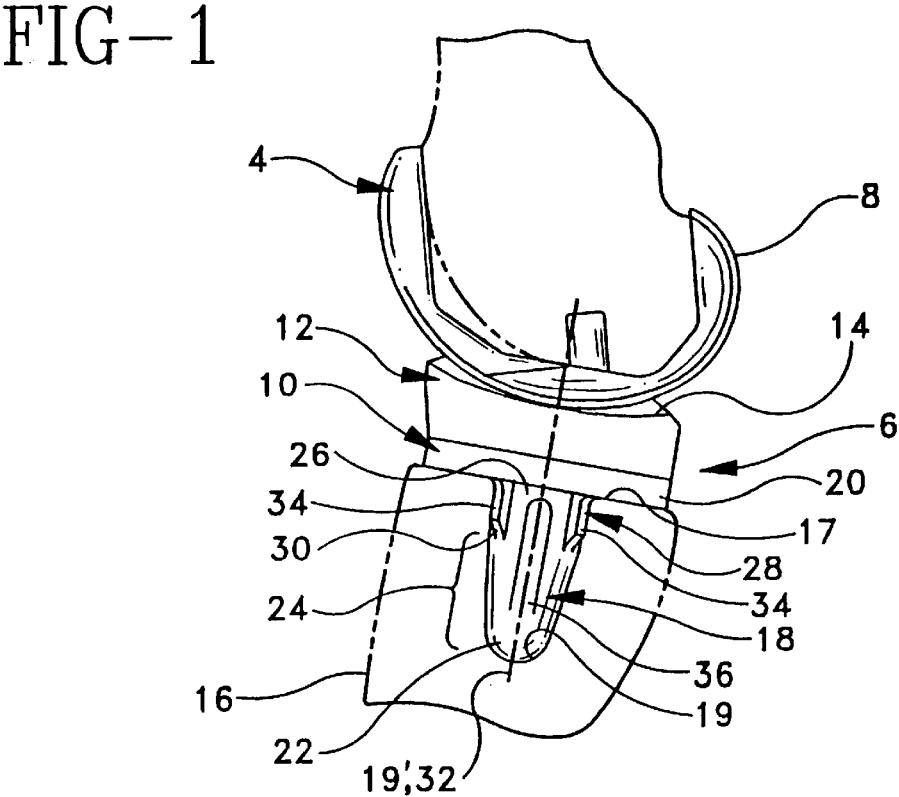
FIG. 1 is a side elevation view of a knee prothesis according to one embodiment of the present invention.

The disclosed embodiment relates to a tibial prosthesis of a knee replacement. This is given by way of example, as other joints may be provided replacement prothesis according to the present invention. The knee replacement prothesis 2 comprises a femoral component 4 and a tibial component 6. The femoral component 4 comprises a hard, corrosion resistant metal. Preferred metals for orthopaedic applications are a cobalt chromium alloy or a ceramic coated, titanium alloy. The femoral component 4 has a polished articulating surface 8. The femoral component is commercially available and does not form any part of the present invention.

The tibial component 6 is a composite structure. It includes a metal fixturing device 10 of the preferred materials mentioned above and a plastic bearing 12 secured to the device 10 in a conventional manner by snap fit or other locking engaging arrangements. The bearing 12 has a bearing surface 14. The device 10 secures the component 6 to the tibia 16. The preferred plastic for orthopaedic applications is ultra high molecular weight polyethylene (UHMWPe).

Figure 6:
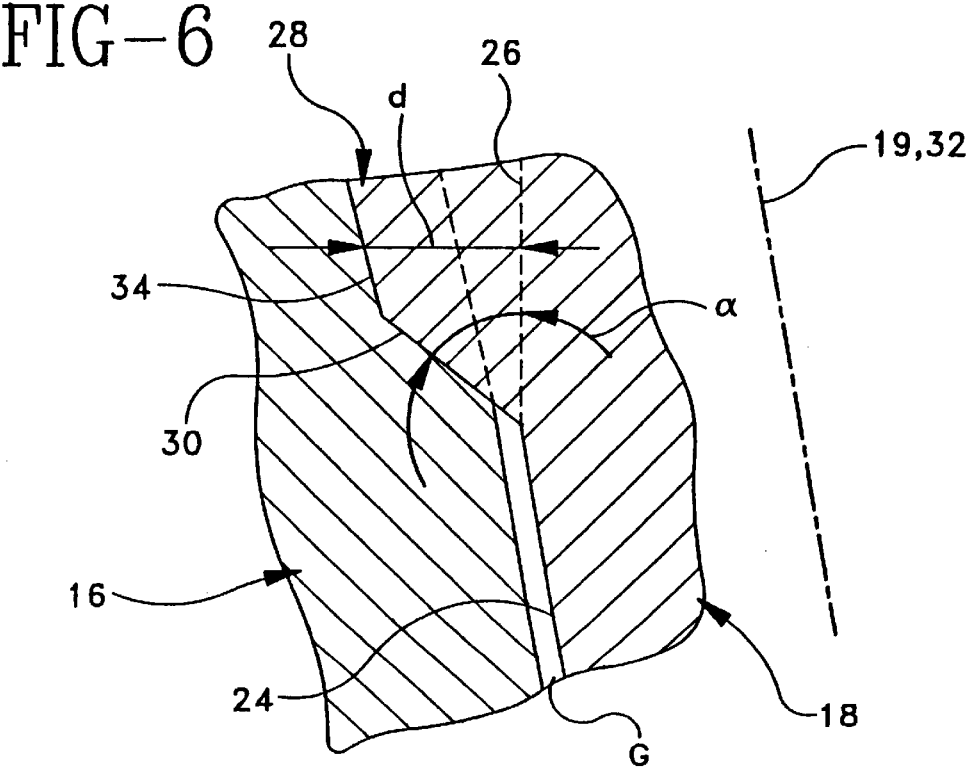
FIG. 6 is a sectional view of the embodiment of the present invention illustrating a fin portion of the stem and bone.

The tibia 16 has a resected surface 17 and a conical cavity 19 for receiving the device 10. The cavity 19 has a longitudinal axis 19' transverse resected surface 17. The stem has a longitudinal axis 32. The device 10 includes a stem 18 and a tray 20. The tray 20 abuts the surface 17 and the stem 18 is received in the cavity 19. The stem 18 includes a distal, spherical end 22, a conical center section 24, and a circular cylindrical proximal section 26. Four fins 28 extend radially outwardly from the cylindrical section 26. The fins 28 are equally spaced about the periphery of the stem. The fins 28 are planar sheets of uniform cross section integral with the stem and tray which are homogeneous without connecting joints. The fins 28 have a tapered end edge 30 which inclines toward the stem 18 longitudinal axis 32 and toward the distal end 22 of the stem. In FIG. 6, the fin 28 inclination α may be about 30° to the stem axis 32. The fins 28 also preferably have inclined outer edges 34 which incline more gradually than edges 30, but in the same general inclination direction toward axis 32 to facilitate penetration of the fins into the tibia during impaction.

The fins 28 are relatively thin, having a thickness preferably of about 2 mm. The fins 28 radially project beyond the stem 18 cylindrical section 26 a distance d, FIG. 6, sufficient to penetrate the tibia a distance of about 1.5 mm when the device 10 is impacted with the tibia as will be described. This penetration amount is significant because it is sufficiently great to provide torsional resistance of the stem about axis 32 without damaging the tibia during impaction. A greater penetration might cause tibia damage whereas a lesser penetration may not provide desired torsional resistance.

In FIG. 6, the conical cavity 19 has a diameter greater than that of the conical section 24 of stem 18 producing a gap G' between the stem and the tibia in cavity 19. Gap G' provides space for cement to bond the device 10 to the tibia. This gap G' causes alignment problems during implantation of the stem and during curing without the presence of fins 28 as will be discussed below.

The torsional resistance of the fins 28 help preclude premature loosening of the device relative to the tibia. At the same time the fin penetration into the tibia is sufficiently small so as to not require forming corresponding channels in the tibia for receiving the fins.

Figure 5:
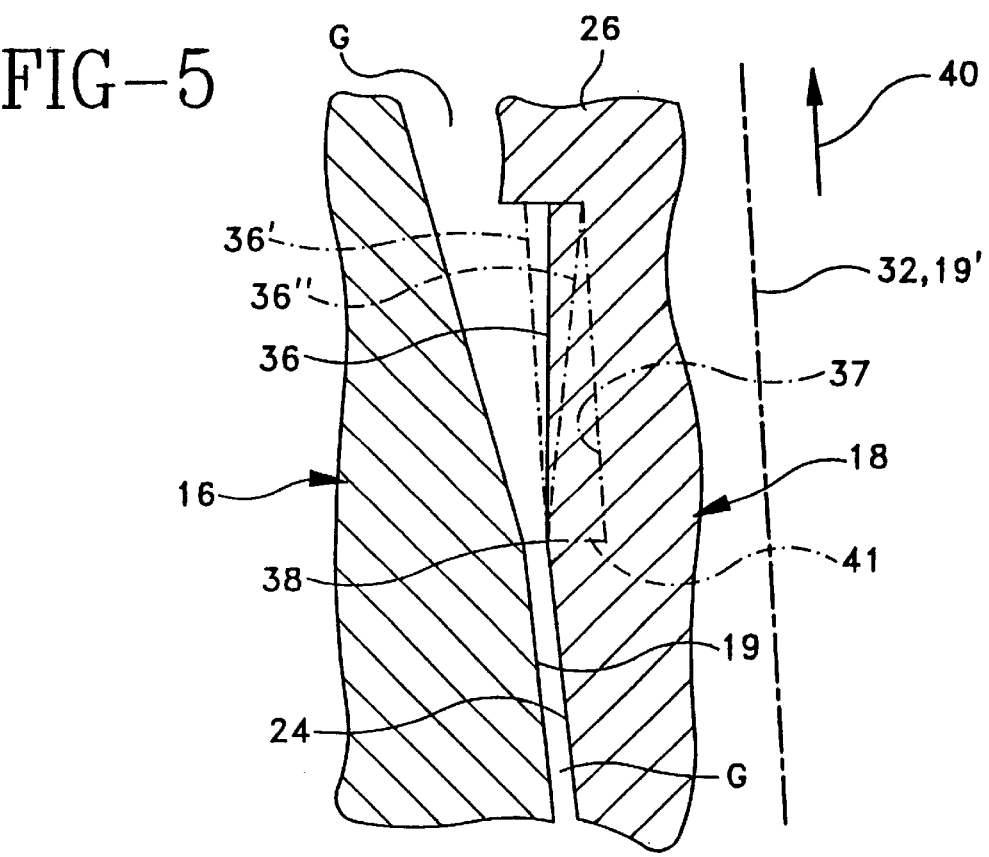
FIG. 5 is a sectional elevation view of the embodiment of the present invention illustrating a channel portion of the stem and bone.

The cylindrical proximal section 26 of stem 18 fitting into the tibia 16 conical cavity 19 provides additional spacing forming a gap G, FIG. 5, between the stem 18 and the tibia 16 in the cavity 19 in the proximal region adjacent the tray 20. This spacing gap G is important as when filled with cement to secure the stem to the tibia, the cement in this region has an increased thickness to assist resisting lateral loading on device 10.

Cut into the center section 24 and cylindrical proximal region at section 26 is an annular array of four channels 36. The channels 36, FIG. 5, are parallel to the axis 32 and intersect the stem conical surface in section 24 at intersection 38. This intersection 38 forms a gradual interface between the channel 36 and the section 24 surface. The channel 36 bottom wall surface may also incline somewhat in an alternative embodiment toward the axis 32 and toward stem end 22, channel 36' (shown in phantom in FIG. 5).

It is important that the channel 36 does not incline toward the axis 32 and proximal section 2 in a direction reverse to that discussed above as shown by channel 36" (shown in phantom), FIG. 5. Such a reverse inclination forms the bottom surface into an undesirable shoulder or undercut interlock in the stem in a direction of axis 32 toward intersection 38 opposite direction 40. In this case the bottom wall of the channel 36" forms the undercut equivalent of a shoulder. If the channel is step recessed into the stem as at channel 37 (shown in phantom) this also can form an undesirable undercut shoulder 41 normal to axis 32.

Such shoulders are not desirable. Cement used to bond the device 10 to the tibia cured in such channels will not release readily should the stem be removed from the cavity 19 in axial direction 40, FIG. 5. The shoulders will capture the cement to the stem and cause the cement to possibly damage the tibia during removal of the stem from the tibia in direction 40.

By making the channel bottom surface parallel to axis 32 or inclined as described at channel 36', the cement in the channel will merely slide out of the channel 36 without harm to the tibia. This is important as occasionally the device 10 may have to be removed from the tibia 16. While four channels are provided, more or fewer may also be used according to a given implementation. The channels 36 serve an important function in contributing to further torsional resistance between the stem 18 and the tibia about axis 32. The cement binds to the pores of the tibia and at the same time being located in the channels 36 provides torsional resistance in the angular direction about axis 32 in this region of the stem.

Figure 3:
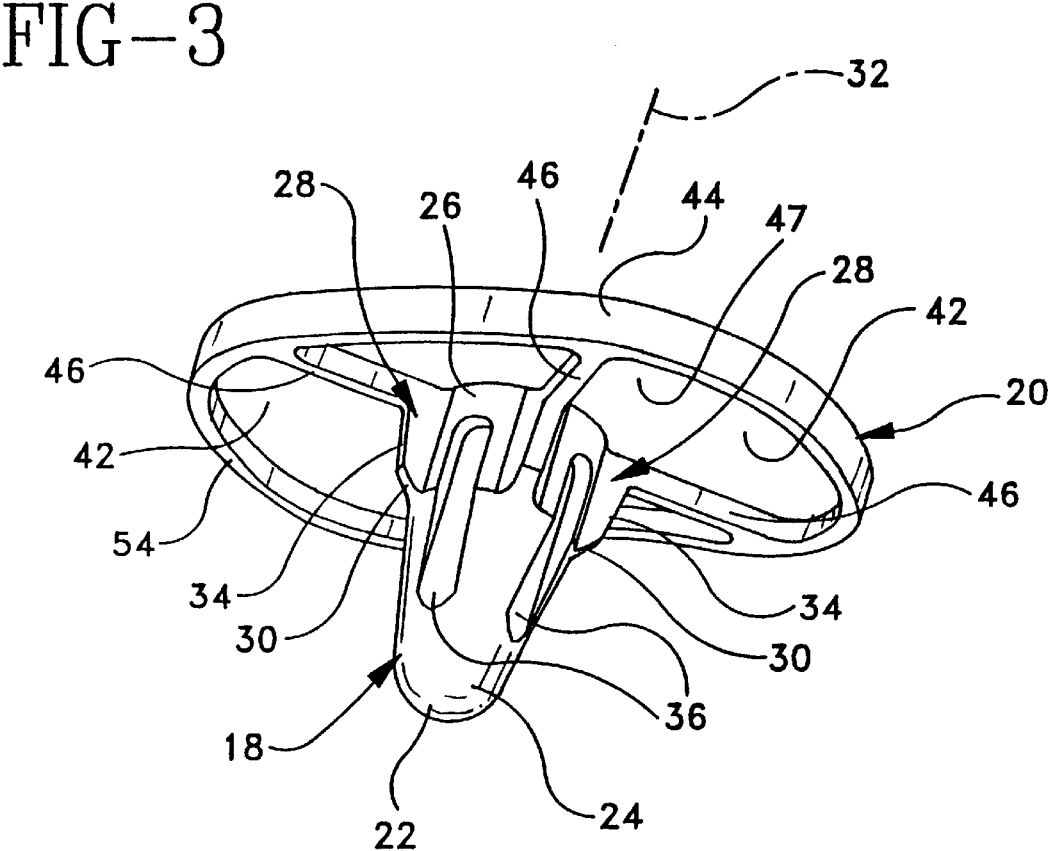
FIG. 3 is an isometric view of a tray used in the embodiments of FIGS. 1 and 2.

The tray 20 underside, FIG. 3, is formed with four annularly spaced recesses 42. The recesses 42 are formed by outer peripheral wall 44 and radially outwardly extending walls 46 depending from the distal side surface 47 of the tray 20. The walls 46 are coplanar extensions of the fins 28 in this embodiment. The recesses 42 are important to provide the major torsional resistance of tray 20 about axis 32 relative to the tibia 16. The recesses 42 have a depth of preferably about 2.5 mm, but could be as low as 1.5 mm or larger.

This depth is important as cement in the recesses 42 also bonds to the pores of the bone at resected surface 17. The bone at the peripheral regions of surface 17 is denser than at the central regions. This denser bone enhances torsional resistance in combination with the recesses 42 at the outer radial regions of the tray 20. The denser bone has higher strength than the less dense inner bone region The torsional resistance is provided by the radial walls 46 which cooperate with the cement (not shown) in the recesses 42 to resist torsion of the tray about axis 32.

In the alternative, the radial walls 46 are not essential to providing torsional resistance where the shape of the tray 20 outer wall is not circular. For example, in FIG. 8, the tray 66 has a somewhat hourglass shape outer wall 70 but could have any other non-circular shape. The outer peripheral wall 70 defines the recess 72 perimeter. The cement in this recess abuts the outer wall 70 to resist torsional loads about axis 68 corresponding to axis 32, FIG. 1.

Figure 8:
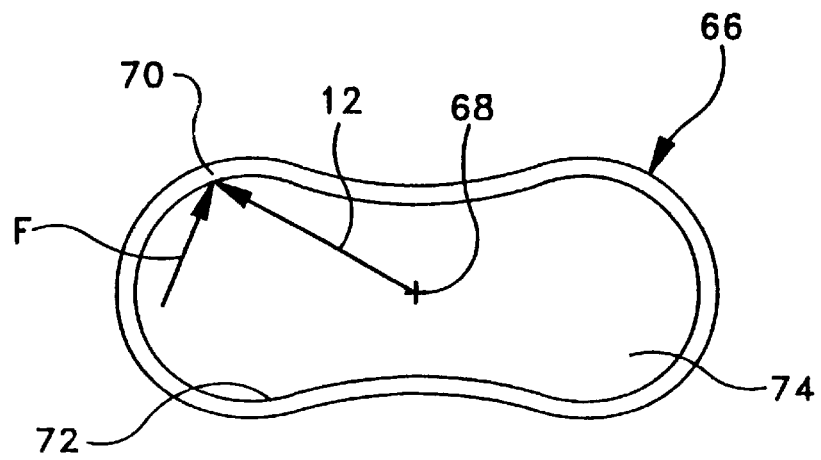
FIG. 8 is a plan bottom view of a tray according to a second embodiment of the present invention.

For example, if a force F were to be applied radial distance R from axis 68, FIG. 8, this force will be directed against wall 70. In a circular outer peripheral wall (not shown), all tangential forces on the cement within the outer periphery will not be directed against a wall resulting in minimum torsional resistance. If the cement loses its adherence to the tray distal surface 74, the tray could merely rotate about the cement on axis 68. This relative rotation of the cement to the tray rotation is resisted in the FIG. 8 embodiment. Thus, if the cement loses its bond to the tray 66 on distal surface 74, the non-circular outer wall 70 will still resist relative rotation of the tray with respect to the cement. This is important in those implementations where a stem is not used and the tray 66 is bonded to the tibia (or other bone) only via the tray 66.

Figure 4:
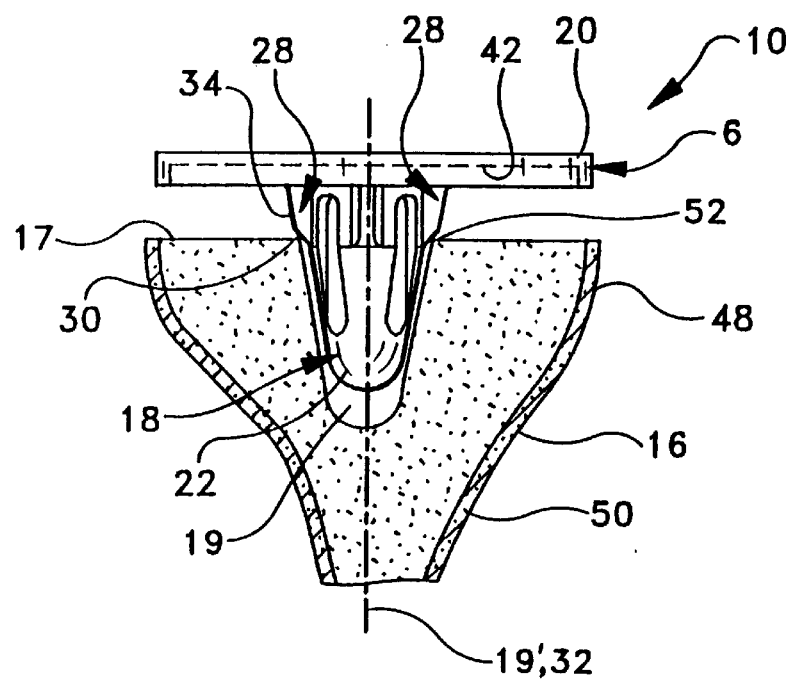
FIG. 4 is a front elevation view of the embodiment of the invention of FIG. 2 showing the tray of FIG. 3 partially inserted into a tibia bone and aligned with the stem receiving cavity in the bone.

As best seen in FIG. 4, to implant the tibial component 6, the proximal tibia 48 is resected to produce a tibial resection surface 17. A circular, conical, cavity 19 is then prepared in the distal tibia 50. This procedure is described in the aforementioned brochure by Frederick F. Buechel. Such a cavity is simple to prepare compared to rectangular, and crossed slot shapes commonly used to provide torque resisting stem fixation in the prior art. Bone cement is then placed in the cavity 19, on stem 18, and into recesses 42. The end 22 of stem 18 is inserted into cavity 19 until the inclined edges 30 of fins 28 engage the outer edge 52 of cavity 19. For clarity, the cement is not shown in FIG. 4.

The inclined edges 30 center and align the stem 18 axis 32 in the cavity 19 substantially on the cavity longitudinal axis 19'. This avoids a shift of the stem 18 to one side of cavity 19 due to gap G', FIG. 5., thereby providing accurate placement alignment of the tibial component 6 relative to the cavity 19. The dimensions of the fins 28 are such that the fins will penetrate into the bone near the cavity on impaction as discussed above. The tibial component 6 is then impacted along its axis 32, driving the fins 28 into the bone of the proximal tibia 48 until the distal side 54 of tray 20 lays flush on the tibial resection surface 17. The tapered outer edges 34 of the fins 28 assist in maintaining substantial coaxial alignment of the axes 19' and 32 during impaction.

The compression produced by the impaction causes the cement to locally penetrate the resected tibial surface 17, and the surface of the conical cavity 19 producing a three dimensional interlock between the bone and the cement. Torsional loads between the tibia 16 and tibial component 6 are primarily resisted by the walls 44 and 46 of recesses 42 in tray 20, and the cement in the recesses 42. The wall 44 assists in the torsional resistance since wall 44 is non-circular in this embodiment and may have the shape of the tray 66 of FIG. 8. These walls carry the bulk of the torsional load. This is because the distances associated with the engaging surfaces of the walls 44 and 42 on the distal side 54 and the cement in the recesses 42 and on tibia surface 17 are relatively large compared to those associated with the engaging surfaces between the stem 18 and cavity 19.

Further, the density of the bone near the peripheral wall 44 between the engaged surfaces of the cement in recesses 42 and surface 17 is much greater than in the region of the stem 18 where the bone is relatively weak. Thus, the bone in the region of the peripheral engaging surfaces is more capable of carrying the torsional loads. The engagement of the fins 28 and the bone of the proximal tibia 48, and the engagement of the channels 36 with the cement also provide some additional torsional load resistance, although to a much lesser degree than the engagement between the tray 20 and cement in recesses 42.

It is preferred that radial walls such as walls 46, FIG. 3 and an outer peripheral wall in a non-circular tray such as wall 70, FIG. 8 be combined in a single tray. However, other implementations may employ only a non-circular outer wall configuration as shown in FIG. 8.

The primary function of the fins 28 is to provide alignment of the tibial component 6 during implantation and to maintain such alignment while the cement is curing. It may be seen, therefore, that a tibial tray 20 with the fixation device 10 disclosed herein is simpler to implant and more effective than stem based torsional resistance fixation devices commonly used in orthopaedics today such as rectangular or other shaped stems.

The surface geometries of fixation device 10 are such that there are no axial extending undercuts in the stem as explained with respect to channels 36" and 37, FIG. 5. Thus the tibial component 6 can easily be withdrawn from the tibia 16 without disturbing the interface between the cement and the bone of the distal tibia 50. Access to the cement is, therefore, provided so as to ease its later removal.

If a three dimension interlock existed in the axial direction 32, e.g., an undercut in the side of the stem 18 as discussed above, or between the tray 20 and the surface 17, between the cement and fixation device 10, removal of the tibial component 6 could produce the loss of significant bone. The cement could fail to break free of the fixation device 10 and the bone of the proximal tibia 48. This could cause fractures within the bone resulting in substantial bone adhering to the cement and thus breaking free of the proximal tibia 48.

Figure 2:
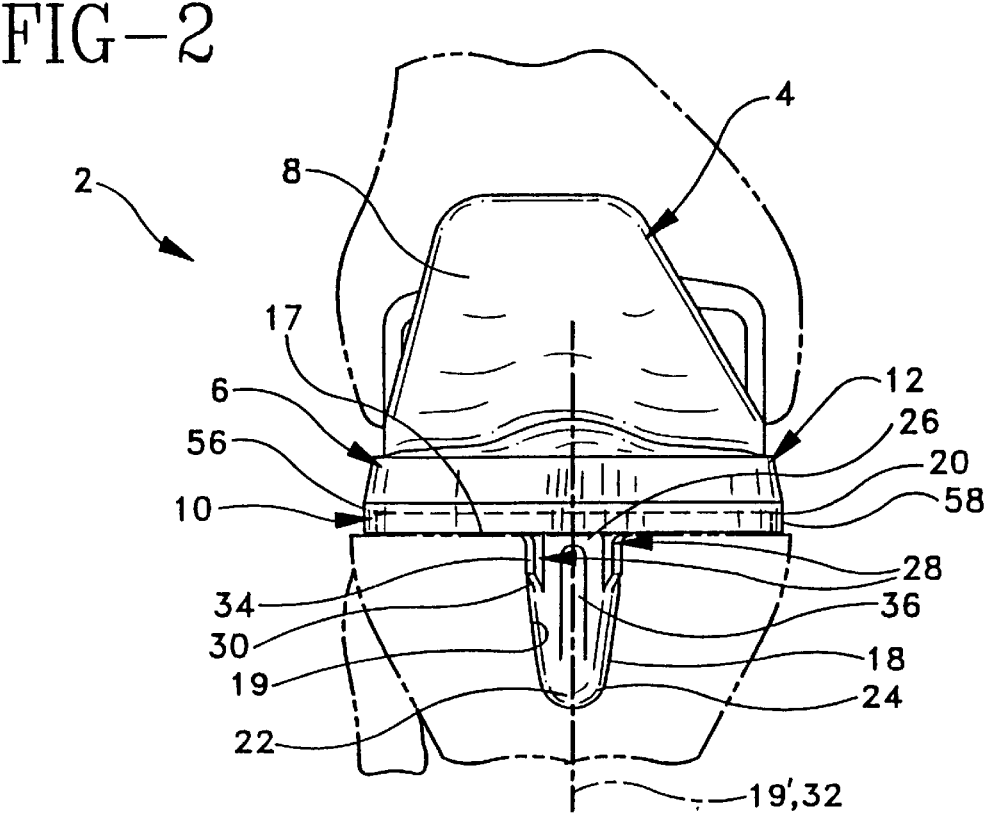
FIG. 2 is a front elevation view of the prothesis of FIG. 1.

The lack of a three dimensional interlock connection between the tibial component 6 and cement in the axial direction as described herein using channels 36, for example, has another important benefit. During normal human activities the load on the tibial tray 20 fluctuates. For example, at one phase of the walking gait the load will be predominantly on the medial condyle of the knee, while at some other phase the load will be predominantly on the lateral condyle. This causes a situation, described in the Pappas et al. brochure mentioned in the introductory portion, where the lateral side 56, FIG. 2, and then the medial side 58 of tray 20, will tend to slightly lift off the resection surface 17.

If a three dimensional axial locking engagement existed between the tray 20 and cement as discussed above in connection with FIG. 5, for example, a tensile stress would be created in the bone when this lift occurred. The cement will pull on the bone in the region of lift. Such tensile stress is undesirable in bone and can result in loss of fixation at the cement to bone interface. This situation is substantially avoided in the present device since the slight lift of a side of the tibial tray will result in a slight separation between the tray and the cement, a less damaging event than separation of the bone and cement. This assumes that the bond between the cement and the tray is weaker than the bond to the bone because of the bone porosity, which porosity is not present in the mating surfaces of the tray cement receiving surfaces.

Figure 7:
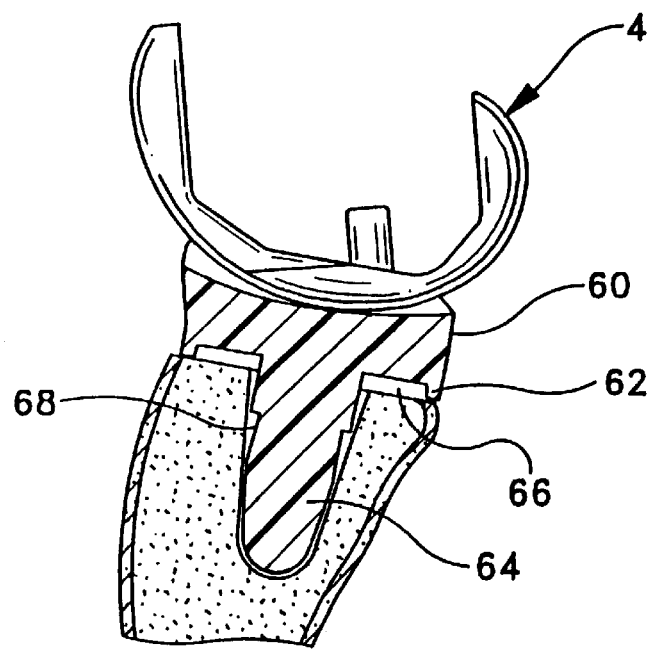
FIG. 7 is a partially in section side elevation view of a second embodiment of the present invention.

In FIG. 7, an alternative embodiment is disclosed wherein the tray 20 and bearing 12 of FIG. 1 are not separate is elements as in FIG. 1, but an integral one piece thermoplastic construction. Bearing 60, tray portion 62 and stem 64 are one piece thermoplastic. Tray portion 62 corresponds substantially to the structure of tray 20, FIGS. 1–4, and stem 64 corresponds substantially to stem 18. In FIGS. 1–4, the tray 20 and stem 18 are formed as a single unitary structure from metal and the bearing is thermoplastic. In FIG. 5, the entire structure is formed as a single thermoplastic unit. Otherwise, the configuration of the recesses 66 in the tray 62, channels 68 and fins (not shown in FIG. 7) are the same in construction as corresponding elements in the embodiment of FIGS. 1–4.

It will occur to one of ordinary skill that various modifications may be made to the disclosed structure whose description is given by way of illustration. It is intended that the scope of the invention is as defined in the appended claims.

What is claimed is:

1. A prosthesis fixturing device for attaching a prosthesis component including a bearing to a bone, said bone having a resected surface, said bone further having a cavity extending therein, said cavity having an edge at the resected surface of the bone, said cavity defining an axis aligned transverse to the resected surface, said resected surface and said cavity being for receiving said device, said device being subject to torque loads about said axis transverse the resected surface, said torque loads tending to loosen the device relative to the bone, said device comprising:

a tray having a first surface for receiving said bearing and a second opposing surface, the first surface of the tray defining an outer periphery;

a stem depending from said tray, said stem having a longitudinal axis, said stem further having a circular cylindrical portion disposed Proximally to said tray and a conical portion depending from the circular cylindrical portion and disposed distally of the tray, said circular cylindrical portion and said conical portion of said stem being dimensioned to be received in said bone cavity such that the second surface of the tray abuts the resected surface of the bone when the stem is received in the bone cavity, said stem further comprising at least three equally spaced projections extending radially outwardly from said stem, said projections having edges disposed distally from said tray, said edges of said projections being inclined toward the stem axis and toward an end of the stem distally of the tray, said edges of said projections being dimensioned to lie on a conical surface of revolution for abutting the cavity edge at said resected surface when said stem is in said cavity for centering said stem in said cavity; and at least one wall dependent from the second surface of the tray for abutting the resected surface of the bone and for forming at least one recessed compartment with the second surface of the tray at a depth of at least 1.50 mm to receive a cement for bonding the tray to the bone at the resected surface, said at least one wall having an outer face aligned with the outer periphery of the first surface of the tray and an inner face aligned substantially parallel to the axis such that said inner face defines a configuration cooperating with the cement for providing resistance to said torque loads on said tray about said axis.

2. The device of claim 1, wherein the outer periphery of the first surface of the tray is non-circular.

3. The device of claim 1, wherein the at least one wall further comprises at least one radial wall extending radially relative to the axis outwardly toward the outer periphery of the first surface of the tray.

4. The device of claim 1, wherein the projections are axially and radially extending planar fins.

5. The device of claim 1, wherein the stem has a plurality of axially extending channels in said circular cylindrical portion terminating in the conical portion.

6. The device of claim 5, wherein the channels have a bottom surface, said stem having a peripheral surface, said channel bottom surfaces intersecting the stem peripheral surface such that the stem tapers radially inwardly in the region from the intersections with the channel bottom surfaces to the stem end distal the tray.

7. The device of claim 6, wherein the stem has a longitudinal axis, the intersections each have a radial dimension to the stem axis, the channel bottom surfaces each having a radial dimension not less than said intersection radial dimension of the corresponding channel.

8. The device of claim 5, wherein the stem has a longitudinal axis, the channel bottom surfaces being parallel to the stem longitudinal axis.

9. The device of claim 1, wherein the projections extend continuously from said stem into said radially walls of the tray, such that said projections center said stem in said cavity and cooperate with said radially walls for resisting torque.

10. The device of claim 1, wherein said at least three equally speed projections comprise four equally spaced projections.

* * * * *